US010893849B2

(12) United States Patent
Satoh et al.

(10) Patent No.: US 10,893,849 B2
(45) Date of Patent: Jan. 19, 2021

(54) ULTRASOUND IMAGE DIAGNOSIS APPARATUS, MEDICAL IMAGE PROCESSING APPARATUS, AND COMPUTER PROGRAM PRODUCT

(71) Applicant: Canon Medical Systems Corporation, Otawara (JP)

(72) Inventors: Shunsuke Satoh, Nasushiobara (JP); Kousuke Namiki, Otawara (JP); Eiji Goto, Utsunomiya (JP); Shouichi Nakauchi, Nasushiobara (JP); Osamu Nakajima, Otawara (JP)

(73) Assignee: Canon Medical Systems Corporation, Otawara (JP)

( * ) Notice: Subject to any disclaimer, the term of this patent is extended or adjusted under 35 U.S.C. 154(b) by 295 days.

(21) Appl. No.: 15/908,047

(22) Filed: Feb. 28, 2018

(65) Prior Publication Data
US 2018/0242952 A1  Aug. 30, 2018

(30) Foreign Application Priority Data

Feb. 28, 2017 (JP) .................................. 2017-037703
Feb. 8, 2018 (JP) .................................. 2018-021326

(51) Int. Cl.
*A61B 8/08* (2006.01)
*G06T 7/00* (2017.01)
(Continued)

(52) U.S. Cl.
CPC .......... *A61B 8/5223* (2013.01); *A61B 8/0841* (2013.01); *A61B 90/37* (2016.02);
(Continued)

(58) Field of Classification Search
CPC ..... A61B 8/5223; A61B 8/0841; A61B 90/37; A61B 2017/00778; A61B 2090/061;
(Continued)

(56) References Cited

U.S. PATENT DOCUMENTS

2006/0056672 A1\* 3/2006 Barth ..................... A61B 8/469
382/131
2009/0306514 A1\* 12/2009 Imamura ................ A61B 8/461
600/458

(Continued)

FOREIGN PATENT DOCUMENTS

| CN | 1243507 C | 3/2006 |
| CN | 103356236 A | 10/2013 |
| JP | 2013-212245 | 10/2013 |

OTHER PUBLICATIONS

Chinese Office Action dated Aug. 31, 2020, issued in Chinese Patent Application No. 201810167506.9.

*Primary Examiner* — Sanjay Cattungal
(74) *Attorney, Agent, or Firm* — Oblon, McClelland, Maier & Neustadt, L.L.P.

(57) ABSTRACT

According to one embodiment, an ultrasound image diagnosis apparatus includes a display and a control circuit. The display is configured to display an ultrasound image generated based on an echo signal of ultrasound waves transmitted to a site to be diagnosed. The control circuit is configured to measure a measurement target on the ultrasound image of the site to be diagnosed displayed on the display. The control circuit performs a definition function to define the distance between a caliper used to measure the measurement target and a guide used to arrange the caliper at the position of the measurement target, a display control function to control the display of the caliper and the guide arranged to be separated by the distance defined such that the caliper and the guide are integrally movable on the ultrasound image, and a measurement function to measure the measurement target using the caliper.

17 Claims, 7 Drawing Sheets

(51) Int. Cl.
*A61B 90/00* (2016.01)
*A61B 17/00* (2006.01)

(52) U.S. Cl.
CPC .......... *G06T 7/0012* (2013.01); *A61B 8/5207* (2013.01); *A61B 2017/00778* (2013.01); *A61B 2090/061* (2016.02); *A61B 2090/378* (2016.02)

(58) Field of Classification Search
CPC ... A61B 2090/378; A61B 8/5207; A61B 8/44; A61B 8/461; G06T 7/0012
See application file for complete search history.

(56) References Cited

U.S. PATENT DOCUMENTS

| | | | |
|---|---|---|---|
| 2013/0261449 A1* | 10/2013 | Tashiro | A61B 8/0891 |
| | | | 600/437 |
| 2014/0276057 A1* | 9/2014 | Lee | A61B 8/54 |
| | | | 600/441 |
| 2016/0051232 A1* | 2/2016 | Yoo | A61B 8/468 |
| | | | 600/440 |
| 2016/0157825 A1* | 6/2016 | Lee | A61B 8/5223 |
| | | | 600/437 |
| 2016/0183923 A1* | 6/2016 | Park | A61B 8/465 |
| | | | 600/443 |
| 2016/0228091 A1* | 8/2016 | Chiang | A61B 8/467 |
| 2017/0090675 A1* | 3/2017 | Lee | A61B 8/469 |
| 2019/0148011 A1* | 5/2019 | Rao | A61B 8/54 |
| | | | 600/437 |

* cited by examiner

ULTRASOUND IMAGE DIAGNOSIS APPARATUS, MEDICAL IMAGE PROCESSING APPARATUS, AND COMPUTER PROGRAM PRODUCT

CROSS-REFERENCE TO RELATED APPLICATION

This application is based on and claims the benefit of priority from Japanese Patent Applications No. 2017-037703, filed on Feb. 28, 2017 and No. 2018-021326, filed on Feb. 8, 2018; the entire contents of which are incorporated herein by reference.

FIELD

Embodiments described herein relate generally to an ultrasound image diagnosis apparatus, a medical image processing apparatus, and a computer program product.

BACKGROUND

In recent years, a subject may be examined by using a modality configured to collect information on the inside of the subject and generate a medical image by imaging the inside of the subject based on the information. Examples of the modality include X-ray CT (computed tomography) systems, MRI (magnetic resonance imaging) equipment, and ultrasonic diagnosis apparatuses.

Besides, based on a medical image acquired by a modality, measurement may be performed using a medical image processing apparatus such as, for example, a workstation to acquire a measurement value. Further, calculation may be performed based on the measurement value using, for example, a clinical application (medical image processing program) implemented in the modality or a medical information processing apparatus to obtain a calculation value.

When a measurement target is measured on a medical image, a caliper for measurement is displayed on the medical image. In addition, a scale for setting a distance from the position of a certain object or a graduated guide line may be displayed together with the caliper.

DETAILED DESCRIPTION

In general, according to one embodiment, an ultrasound image diagnosis apparatus includes a display and a control circuit. The display is configured to display an ultrasound image generated based on an echo signal of ultrasound waves transmitted to a site to be diagnosed. The control circuit is configured to measure a measurement target on the ultrasound image of the site to be diagnosed displayed on the display. The control circuit performs a definition function to define the distance between a caliper used to measure the measurement target and a guide used to arrange the caliper at the position of the measurement target, a display control function to control the display of the caliper and the guide arranged to be separated by the distance defined such that the caliper and the guide are integrally movable on the ultrasound image, and a measurement function to measure the measurement target using the caliper.

Illustrative embodiments are described in detail with reference to the drawings.

In the following, for example, an ultrasound image diagnosis apparatus is described as being used to measure a measurement target on a medical image using a caliper and a guide. The ultrasound image diagnosis apparatus is an example of a medical image diagnosis apparatus capable of noninvasively examining the internal structure and blood flow state of a subject.

The ultrasound image diagnosis apparatus is configured to transmit ultrasound waves toward the inside of a subject from an ultrasound probe having transducers (piezoelectric transducers) at the tip, and receive reflected waves caused by acoustic impedance mismatch in live subject through the transducers. The ultrasound image diagnosis apparatus generates an ultrasound image based on the received signal.

[Configuration of Ultrasound Image Diagnosis Apparatus]

Figure 1:
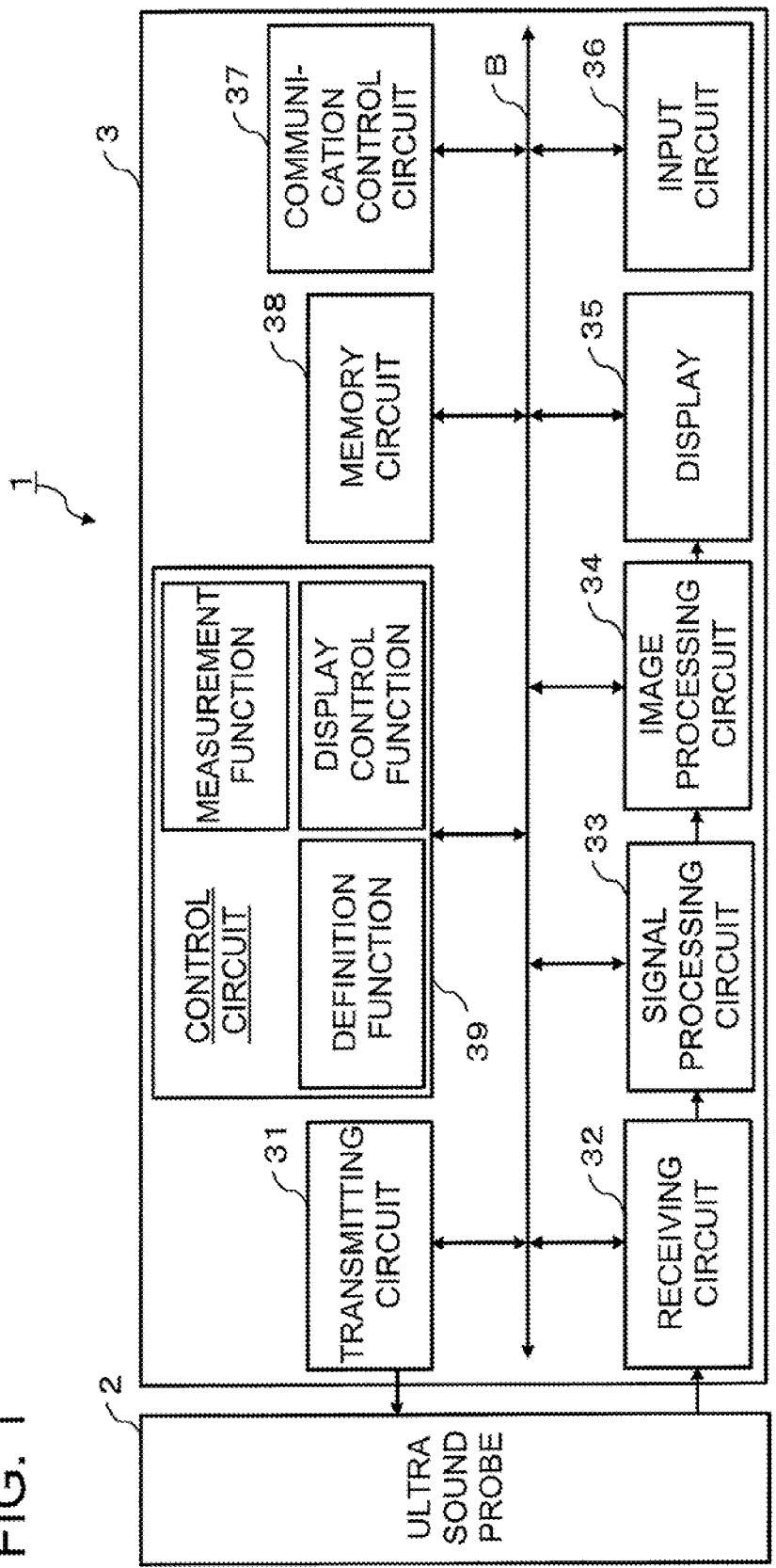
FIG. 1 is a block diagram illustrating the overall configuration of an ultrasound image diagnosis apparatus according to an embodiment.

FIG. 1 is a block diagram illustrating the overall configuration of an ultrasound image diagnosis apparatus 1 according to an embodiment. As illustrated in FIG. 1, the ultrasound image diagnosis apparatus 1 includes an ultrasound probe 2 configured to transmit/receive ultrasound waves (transmitted and received waves) to/from a subject, and a main body 3 to which the ultrasound probe 2 is detachably connected.

The ultrasound probe 2 is configured to transmit ultrasound waves into the subject through each of ultrasound transducers to scan a scan area, and receive reflected waves from the subject as echo signals. Examples of the scan include various types of scans such as B mode scan and Doppler mode scan. Besides, examples of the ultrasound probe 2 include a sector scan probe, a linear scan probe, a convex scan probe and the like, and one of them is arbitrarily selected according to a diagnosis site.

The main body 3 includes a transmitting circuit 31, a receiving circuit 32, a signal processing circuit 33, an image processing circuit 34, a display 35, and an input circuit 36. The transmitting circuit 31 is configured to transmit a drive signal to the ultrasound probe 2. The receiving circuit 32 is configured to receive echo signals from the ultrasound probe 2. The signal processing circuit 33 is configured to process the echo signals. The image processing circuit 34 is configured to generate an ultrasound image. The display 35 is configured to display various images including the ultrasound image generated. The input circuit 36 is configured to receive an input signal as being operated by an operator such as an examiner. The main body 3 further includes a communication control circuit 37 configured to control the exchange of signals with other devices (not illustrated), a memory circuit 38, and a control circuit 39 configured to control each part. These circuits are connected to a bus B and can exchange various signals. Described below are detailed functions of each circuit.

Under the control of the control circuit 39, the transmitting circuit 31 generates a drive signal for causing the ultrasound probe 2 to generate ultrasound waves, i.e., an electric pulse signal (hereinafter referred to as "drive pulse") to be applied to each of the piezoelectric transducers. The transmitting circuit 31 transmits the drive pulse to the ultrasound probe 2. The transmitting circuit 31 includes circuits such as, for example, a reference pulse generating circuit, a delay control circuit, a drive pulse generating circuit, and the like (not illustrated), and each circuit performs the functions mentioned above.

The receiving circuit 32 receives an echo signal, i.e., received signal from the ultrasound probe 2. The receiving circuit 32 performs phasing addition on the received signal, and outputs the resultant signal to the signal processing circuit 33.

The signal processing circuit 33 generates various types of data using the received signal from the ultrasound probe 2 fed by the receiving circuit 32, and outputs the data to the image processing circuit 34 and the control circuit 39. The signal processing circuit 33 includes, for example, a B mode processing circuit (or Bc mode processing circuit), a Doppler mode processing circuit, a color Doppler mode processing circuit, and the like (not illustrated). The B mode processing circuit visualizes amplitude information of the received signal, and generates data based on a B mode signal. The Doppler mode processing circuit extracts Doppler shift frequency component from the received signal, and applies fast Fourier transform (FFT) or the like thereto, thereby generating Doppler signal data of blood flow information. The color Doppler mode processing circuit visualizes the blood flow information based on the received signal, and generates data based on a color Doppler mode signal.

The image processing circuit 34 generates two-dimensional or three-dimensional ultrasound images related to the scan area based on the data supplied from the signal processing circuit 33. For example, the image processing circuit 34 generates volume data related to the scan area from the supplied data. Then, from the volume data generated, the image processing circuit 34 generates data of a two-dimensional ultrasound image by multi-planar reconstruction (MPR) and data of a three-dimensional ultrasound image by volume rendering. The image processing circuit 34 outputs the two-dimensional or three-dimensional ultrasound image to the display 35. Examples of the ultrasound image include a B mode image, a Doppler mode image, a color Doppler mode image, an M mode image, and the like.

The display 35 displays various images such as an ultrasound image generated by the image processing circuit 34 and an operation screen (e.g., graphical user interface (GUI) configured to receive various instructions from the operator) under the control of the control circuit 39. As the display 35, for example, a liquid crystal display (LCD), an organic electroluminescence (EL) display, or the like can be used.

The input circuit 36 receives various input operations made by the operator to provide, for example, an instruction to display an image or switch images, designation of the mode, various settings, and the like. For example, GUI, input devices such as buttons, a keyboard, a trackball, a touch panel displayed on the display 35, or the like can be used as the input circuit 36.

Incidentally, in the embodiment, the display 35 and the input circuit 36 are each described as one constituent element of the ultrasound image diagnosis apparatus 1 as illustrated in FIG. 1; however, it is not so limited. The display 35 need not necessarily be a constituent element of the ultrasound image diagnosis apparatus 1, but may be, for example, a display separate from the ultrasound image diagnosis apparatus 1. The input circuit 36 may be a touch panel displayed on the separate display.

The communication control circuit 37 enables the ultrasound image diagnosis apparatus 1 to communicate with medical image diagnosis apparatuses (modalities), servers, medical image processing apparatuses, and the like (not illustrated) each connected to a communication network (not illustrated). Information and medical images exchanged between the communication control circuit 37 and other devices via the communication network may be in conformity with any standards such as digital imaging and communication in medicine (DICOM) and the like.

The memory circuit 38 is formed of, for example, a semiconductor or a magnetic disk. The memory circuit 38 stores programs to be executed by the control circuit 39, data, a combination of a caliper and a guide used for measurement process, and the like.

The control circuit 39 comprehensively controls each part of the ultrasound image diagnosis apparatus 1. The control circuit 39 causes the display 35 to display the ultrasound image generated by the image processing circuit 34. Further, when diagnosis is performed by the operator using the ultrasound image diagnosis apparatus 1, the control circuit 39 performs a process of measuring a measurement target at the site to be diagnosed on the ultrasound image displayed on the display 35.

The control circuit 39 performs a definition function, a display control function, and a measurement function. The definition function is a function of defining the shape and positional relationship of a group of calipers and guides used for measuring a measurement target at the site to be diagnosed on the ultrasound image. When the measurement process is performed, the caliper and the guide are used integrally, and therefore the caliper and the guide are defined as one unit.

When a measurement target is measured, the caliper is used to specify the measurement range. For example, by arranging the caliper so as to pinch a blood vessel illustrated in an ultrasound image, the diameter of the blood vessel is measured. In addition, the guide is used to arrange the caliper at a position to be measured. Specifically, the guide is arranged by the operator at the position of the index provided near the measurement target displayed on the ultrasound image.

When a measurement target is measured, the operator selects a caliper and a guide having a shape suitable for the measurement target. Also, a distance between the caliper and the guide is determined in advance for each measurement target. The distance is defined, for example, in the measurement procedure determined by the academy to measure the measurement target. The distance may also be defined statistically according to the conditions such as the race, place of residence, gender, and the like of the subject. Further, the display angle between the caliper and the guide is also defined.

As described above, the shape of the caliper and the guide and the positional relationship thereof are defined for each measurement target. The definition is stored in the memory circuit 38. In the following, examples of the definition for the caliper and the guide by the control circuit 39 are described with reference to the drawings.

Figure 2:
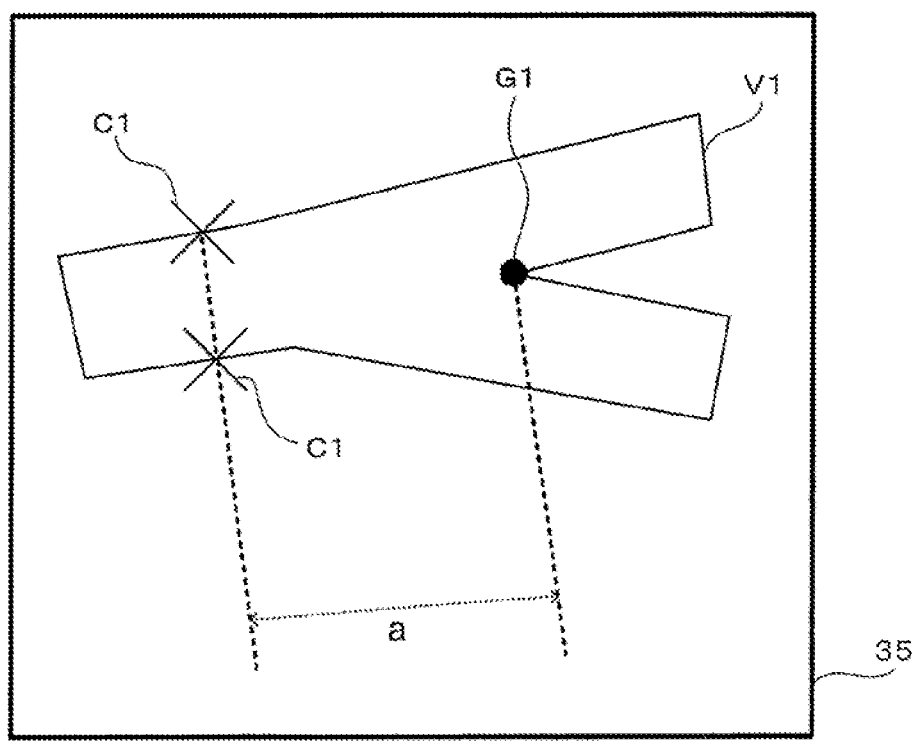
FIG. 2 is an explanatory diagram illustrating a first example in which a caliper and a guide are arranged with respect to a measurement target according to the embodiment.

FIG. 2 is an explanatory diagram illustrating a first example in which a caliper and a guide are arranged with respect to a measurement target according to the embodiment. In FIG. 2, a blood vessel V1 is displayed on the display 35 as a measurement target at the site to be diagnosed. The blood vessel V1 is branched. FIG. 2 illustrates the state of measuring the outer diameter of the blood vessel V1.

Referring to FIG. 2, the guide G1 is placed at the branch portion. In FIG. 2, the guide G1 is indicated by a circular mark. On the other hand, the caliper C1 is located at a position separated from the guide G1 by a distance a. The caliper C1 is indicated by a cross (x) in two places. This is for measuring the outer diameter of the blood vessel V1 as the measurement target, and thus the caliper C1 is arranged so as to pinch the blood vessel V1.

In this case, the control circuit 39 defines the display shapes of the caliper C1 and the guide G1 so as to be suitable for measuring the outer diameter of the blood vessel V1 by its definition function. In addition, the control circuit 39 defines the positional relationship such that the caliper C1 is arranged at a position separated from the guide G1 by a predetermined distance (in this example, distance a).

Figure 3:
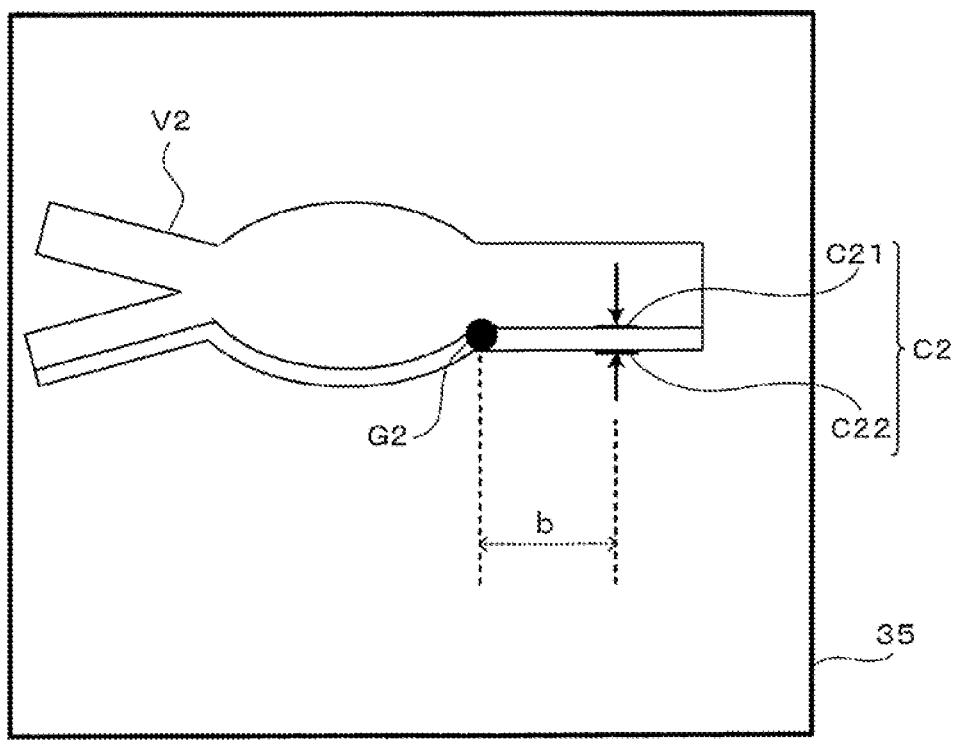
FIG. 3 is an explanatory diagram illustrating a second example in which a caliper and a guide are arranged with respect to a measurement target according to the embodiment.

FIG. 3 is an explanatory diagram illustrating a second example in which a caliper and a guide are arranged with respect to a measurement target according to the embodiment. In FIG. 3, a blood vessel (carotid artery) V2 is displayed on the display 35 as a measurement target at the site to be diagnosed. The carotid artery V2 is branched, and further, a bulge seeming to be a carotid sinus is seen near the branch portion. FIG. 3 illustrates the state of measuring the thickness of the blood vessel wall of the carotid artery V2.

In the case of measuring the thickness of the blood vessel wall of the carotid artery V2, as illustrated in FIG. 3, the guide G2 is arranged not at the branch portion of the blood vessel but at a position in front of the carotid sinus, where the blood vessel starts bulging toward the branch portion. Similarly to the guide G1 illustrated in FIG. 2, the guide G2 is represented by a circular mark.

On the other hand, the caliper C2 is arranged at a position separated from the guide G2 by a distance b. The caliper C2 is represented by two plate-like marks, which are arranged at positions facing each other with a blood vessel wall to be measured interposed therebetween. The thickness of the blood vessel wall can be measured by placing the caliper C2 so as to sandwich the blood vessel wall and measuring the distance between the two plate-like marks (C21, C22) constituting the caliper C2.

In this manner, the control circuit 39 defines the display shapes of the caliper C2 and the guide G2 so as to be suitable for measuring the thickness of the blood vessel wall of the carotid artery V2 by its definition function. In addition, the control circuit 39 defines the positional relationship such that the caliper C2 is arranged at a position separated from the guide G2 by a predetermined distance (in this example, distance b).

Examples of the definition for the caliper and the guide by the control circuit 39 are described above with reference to the explanatory views illustrated in FIGS. 2 and 3. However, how to hold the ultrasound probe 2 (how to apply it to the subject) varies depending on the operator. That is, for example, to measure a branched blood vessel such as carotid artery, some operators may hold and operate the ultrasound probe 2 such that the branch portion is displayed on the right side on the screen, while others may hold and operate the ultrasound probe 2 such that the branch portion is displayed on the left side on the screen.

Figure 4:
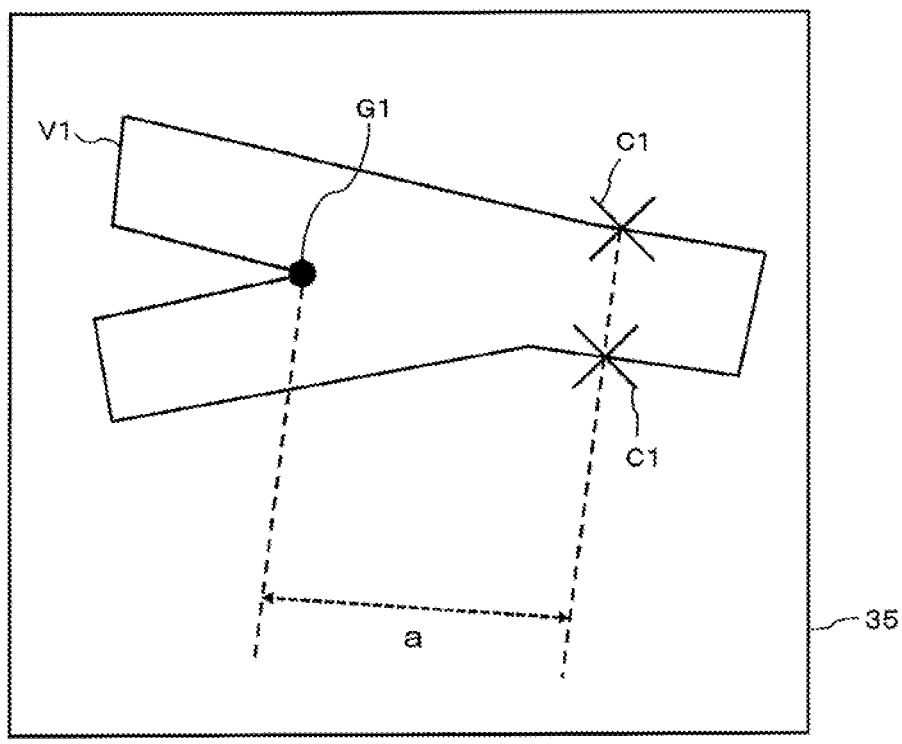
FIG. 4 is an explanatory diagram illustrating the arrangement of the caliper and the guide when the measurement target is reversed according to the embodiment.

FIG. 4 is an explanatory diagram illustrating the arrangement of the caliper and the guide when the measurement target is reversed according to the embodiment. In FIG. 4, the blood vessel V1 is displayed on the display 35 as a measurement target at the site to be diagnosed. The blood vessel V1 is branched. Regarding the display direction of the blood vessel V1 illustrated in FIG. 4, the branch portion of the blood vessel is displayed on the left side on the screen. It can be seen that the direction of the blood vessel V1 is reversed as compared to that of FIG. 2.

As described above, the direction of the measurement target displayed on the display 35 varies depending on how the operator holds the ultrasound probe 2. If the display of the caliper and the guide does not vary despite the reversal of the direction of the measurement target, the caliper and the guide cannot fulfill their original functions. Therefore, the direction of the caliper and the guide is changed according to the direction of the measurement target displayed on the display 35.

The direction of the caliper and the guide may be changed manually by the operator or automatically by the ultrasound image diagnosis apparatus 1 according to the direction of the measurement target. In the former case, while viewing the display on the display 35, the operator operates the input circuit 36 as appropriate according to the direction of the measurement target to change the direction of the caliper and the guide. In the latter case, the control circuit 39 figures out the direction of the measurement target displayed on the display 35 and changes the direction of the caliper and the guide according to the direction of the measurement target. In this case, to figure out the direction of the measurement target, for example, the measurement target displayed on the display 35 may be recognized as an image and the direction thereof may be identified. It is relatively easy to figure out the direction. That is, there is one lumen (common carotid artery) on one side and there are two lumens (external carotid artery, internal carotid artery) on the other side with respect to the branch portion as a boundary. Therefore, it is only necessary to recognize the image of the luminal structure and there is no difficulty.

As described above, the directions of the caliper and the guide are also changed as appropriate according to the direction of the measurement target. Thereby, by performing the display so as not to give the operator a sense of incongruity, and the measurement process can be performed quickly and easily using the caliper and the guide without causing erroneous recognition by the operator.

Figure 5:
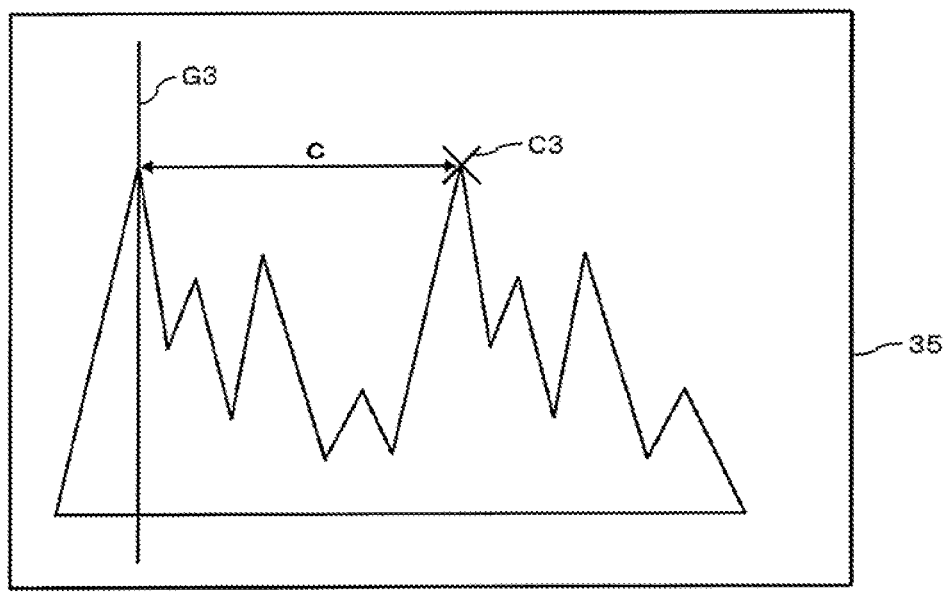
FIG. 5 is an explanatory diagram illustrating a third example in which a caliper and a guide are arranged with respect to a measurement target according to the embodiment.

FIG. 5 is an explanatory diagram illustrating a third example in which a caliper and a guide are arranged with respect to a measurement target according to the embodiment. FIG. 5 illustrates the Doppler waveform of received ultrasound waves, which is represented in a mountain shape. The height of the Doppler waveform indicates the velocity of blood flow at the site to be diagnosed. In the case of rapid blood flow, the Doppler waveform is displayed in a high mountain shape, while in the case of slow blood flow, it is displayed in a low mountain shape. That is, the velocity of blood flow is represented by the vertical axis, and the passage of time is represented by the horizontal axis (time axis). FIG. 5 illustrates the case of measuring the maximum value or the minimum value in the blood flow until a predetermined time has elapsed from reference time, or measuring the value at the position where the caliper is placed.

In FIG. 5, a guide G3 is arranged at the reference time. Since the guide G3 indicates the reference time in this manner, for example, differently from the guides G1 and G2 described with reference to FIGS. 2 and 3, the guide G3 is indicated by a bar perpendicular to the time axis represented by the horizontal axis. On the other hand, a caliper C3 is represented by a cross (x) and is arranged at a position separated from the guide G3 by time c. That is, in this example, the measurement target is the maximum value, the minimum value, or the like during a period from the reference time until a predetermined time has elapsed at the site to be diagnosed. Accordingly, the distance between the guide G3 and the caliper C3 is defined on the time axis.

In this manner, the control circuit 39 defines the display shapes of the caliper C3 and the guide G3 so as to be suitable for measuring the maximum value in the blood flow during a period from the reference time until a predetermined time has elapsed by its definition function. In addition, the control circuit 39 defines the positional relationship such that the caliper C3 is arranged at a position separated from the guide G3 by a predetermined distance (in this example, time c).

The predetermined distance between the guide G (hereinafter the guides G1 to G3 are collectively referred to as "guide G" as appropriate) and the caliper C (hereinafter the calipers C1 to C3 are collectively referred to as "caliper C" as appropriate) is a value actually measured in the subject. That is, the distance, between the guide G1 and the caliper C1 and the distance between the guide G2 and the caliper C2 are the actual dimensions obtained by measuring the measurement target in the site to be diagnosed in the subject. Besides, the predetermined distance between the guide G3 and the caliper C3 on the time axis is real time. The predetermined distance between the guide and the caliper on the time axis may be set such that the caliper is temporally ahead (in the future) with reference to the guide, or conversely, the caliper is temporally behind (in the past) with reference to the guide.

The display control function of the control circuit 39 involves a function of causing the display 35 to display an ultrasound image illustrating a measurement target at the site to be diagnosed. Further, when the operator instructs to measure the measurement target at the site to be diagnosed through the input circuit 36, the control circuit 39 displays the caliper C and the guide G on the ultrasound image displayed on the display 35 based on an operation signal corresponding to the instruction by the display control function.

In order to display the caliper C and the guide G on the ultrasound image based on, for example, information indicating a photographed site possessed by the ultrasound image, the control circuit 39 retrieves the caliper C and the guide G stored in the memory circuit 38. The caliper C and the guide G are stored in the memory circuit 38 with respect to each measurement target. However, depending on the measurement target, the memory circuit 38 may store a plurality of combinations of the caliper C and the guide G. When there are a plurality of combinations of the caliper C and the guide G, the control circuit 39 retrieves all the combinations, and displays them on the display 35.

When the caliper C and the guide G are selected by the operator, the control circuit 39 make a preparation for displaying the caliper C and the guide G selected on the display 35. As described above, the distance between the caliper C and the guide G is an actual measurement value indicated by actual size or real time. Therefore, when the caliper C and the guide G are directly displayed on the display 35, they may not match with the display scale of the ultrasound image displayed behind.

For this reason, the control circuit 39 calculates the size of the guide and the caliper to be displayed according to the display scale of the ultrasound image displayed on the display 35, and changes the size of the guide and the caliper selected. With this process, when the operator places the guide G, the caliper C is arranged at the position of the measurement target on the screen displayed, that is, the position to actually measure.

As described above, both the caliper C and the guide G need not necessarily be displayed on the display 35 at the same time. However, when either one of the caliper C or the guide G is displayed, only the guide G is displayed. This is because the guide G is used for placing the caliper C at a position to be measured.

However, not only in the case where both the caliper C and the guide G are displayed on the ultrasound image, but also in the case where only the guide G is displayed, when the guide G is moved according to an operation instruction from the operator, they are moved together on the ultrasound image. This is because, as described above, the caliper C and the guide G are defined as a single unit. Note that, even if they are moved together, it does not mean that they are always simultaneously displayed on the ultrasound image.

Specifically, in the measurement process, not only when the caliper C and the guide G are displayed on the ultrasound image and moved together, but also, for example, when only the guide G is displayed, the caliper C is also moved although it is not displayed. In this manner, the caliper C and the guide G are integrally moved irrespective of whether it is displayed. Therefore, by arranging the guide G at a position serving as the index, the caliper C can be arranged at a predetermined distance from the guide G or at a position spaced apart by a predetermined distance on the time axis.

Then, the position where the caliper C is arranged is the position of the measurement target. In this manner, the arrangement position of the caliper C is determined in relation to the guide G. For example, referring to FIG. 2 as an example, the caliper C1 and the guide G1 are moved together on the ultrasound image displayed on the display 35 while always maintaining the positional relationship in which they are separated by a predetermined distance a.

When the caliper C1 and the guide G1 are rotated, they are also rotated together. Incidentally, the rotational axis for rotating the caliper C1 and the guide G1 may be on the caliper C1, the guide G1, or between the both.

The control circuit 39 moves the guide G based on the operation of the operator to place the guide G displayed on the ultrasound image at a position serving as the index. The index indicates a position where the guide is to be placed in order to arrange the caliper C at the position of the measurement target, and is provided, for example, in the measurement procedure recommended by the academy. The index is not displayed on the ultrasound image. The operator specifies the position of it with reference to the ultrasound image. However, for example, the index may be displayed on the ultrasound image in advance.

Since the distance between the guide G and the caliper C is defined in advance, when the arrangement position of the guide G is determined on the ultrasound image, the caliper C is arranged at the position of the measurement target at the same time. However, although the caliper C is placed at the position of the measurement target, it is not always arranged so as to be capable of measurement.

An example is given with reference to FIG. 3 illustrating the second example in which the guide G2 and the caliper C2 are arranged with respect to the measurement target. First, the guide G2 is arranged according to the position of the index. After the guide G2 is arranged, the caliper C2 is arranged at a position separated from the guide G2 by a predetermined distance b. In this case, the thickness of the blood vessel wall of the carotid artery V2 is measured. In order to properly measure the blood vessel wall, it is required to pinch the blood vessel wall with the caliper C2 (the calipers C21 and C22) represented by a pair of plate-like marks with an appropriate distance. Therefore, when the caliper C2 is arranged at the position of the measurement target, adjustment is not particularly necessary as long as it is arranged at a position suitable for measuring the thickness of the blood vessel wall. On the other hand, when the caliper C2 is not arranged at an appropriate position, it is necessary to adjust the distance between the caliper C21 and the caliper C22 and the angle thereof in order to pinch the blood vessel wall.

Having determined the position of the guide G on the ultrasound image, the control circuit 39 receives an input signal from the operator who sets the inclination (angle) of the caliper C and the guide G according to the position of the measurement target, and displays the caliper C and the guide G at the set angle.

Either one of the determination of the arrangement position of the guide G on the ultrasound image and the setting of the angle of the caliper C and the guide G may be performed before the other. As described above, the caliper C and the guide G can be integrally moved on the display 35 irrespective of the measurement target, and the angle can be changed irrespective of the determination of the arrangement position of the guide G.

The control circuit 39 further has the function of measuring the measurement target at which the caliper C is arranged. In the embodiment, by arranging the guide G according to the position of the index on the ultrasound image, the caliper C is also arranged at the position of the measurement target at the same time. Thus, the measurement process may be performed automatically in the ultrasound diagnostic imaging apparatus 1 as the guide G is arranged.

Alternatively, in order to secure the time to allow the operator to check the arrangement position of the caliper C or the like after the guide G is placed, the measurement process may be started in response to the input of a measurement process start signal from the operator after the guide G is placed. In other words, after the arrangement position of the caliper C is determined, the operation is not automatically shifted to the measurement process, and the operator may be provided with an opportunity to determine whether the position of the caliper C is appropriate. In this case, the operator operates the input circuit 36 by for starting the measurement process, and the control circuit 39 starts the measurement process in response to an input signal based on the operation.

For example, the definition function, display control function, and measurement function of the control circuit 39 can be realized by a computer program that is executed by a processor and stored in a predetermined memory, the memory circuit 38, or the like. The term "processor" as used herein refers to a circuit such as, for example, a dedicated or general central processing unit (CPU) arithmetic circuit (circuitry), an application specific integrated circuit (ASIC), a programmable logic device including a simple programmable logic device (SPLD) and a complex programmable logic device (CPLD), a field programmable gate array (FPGA), or the like.

The processor reads out, for example, a program stored in the memory circuit 38 or directly incorporated in the circuit of the processor and execute it, thereby realizing the functions. The recording circuit for storing the program may be provided for each processor or may be a storage that stores a program corresponding to the functions of the signal processing circuit 33 illustrated in FIG. 1. Further, the configuration of the memory circuit 38 illustrated in FIG. 1 may be adopted to store the program. The memory circuit is formed of a storage device like a semiconductor memory and a magnetic disk such as a general random access memory (RAM) and a hard disc drive (HDD).

[Operation]

Figure 6:
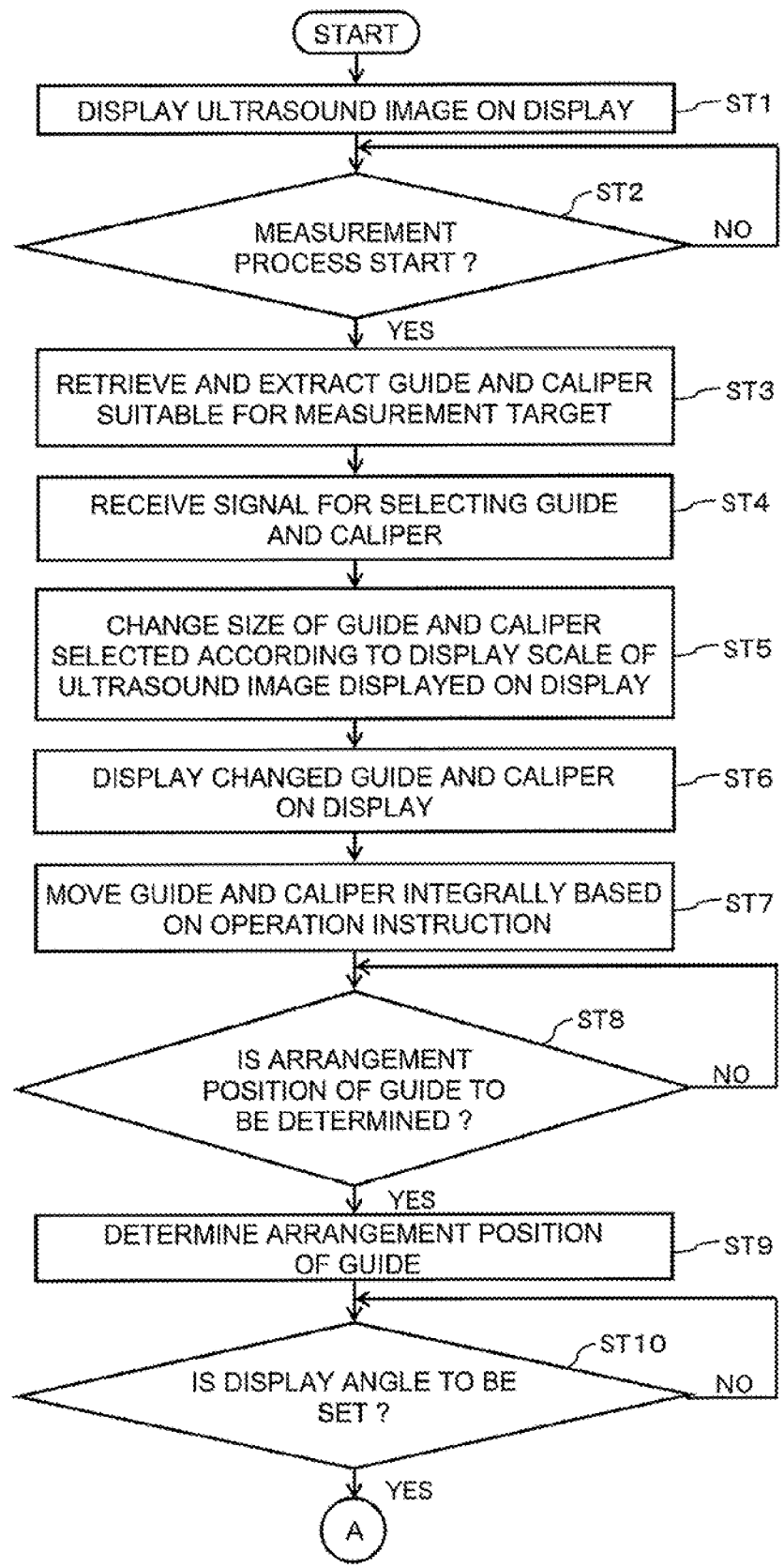
FIG. 6 is a flowchart illustrating the operation of measuring the measurement target on a medical image using the caliper and the guide according to the first embodiment.
Figure 7:
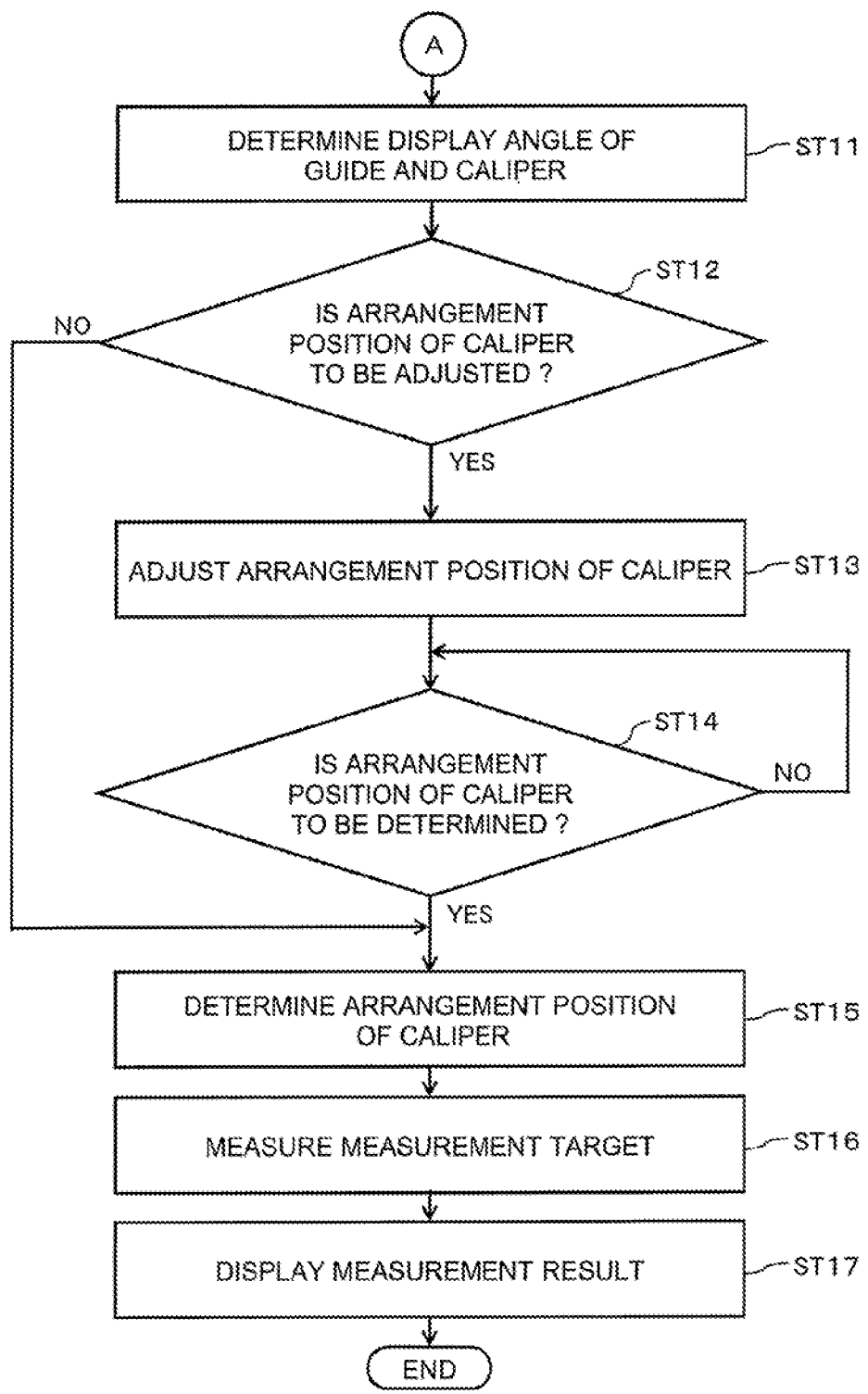
FIG. 7 is a flowchart illustrating the operation of measuring the measurement target on a medical image using the caliper and the guide according to the first embodiment.

Next, with reference to FIGS. 6 and 7, a description is given of the operation of the ultrasound image diagnosis apparatus 1 for measuring a measurement target. FIGS. 6 and 7 are flowcharts illustrating the operation of measuring a measurement target on a medical image using the guide G and the caliper C according to the embodiment.

First, the control circuit 39 causes the display 35 to display an ultrasound image illustrating a measurement target at the site to be diagnosed through the display control function (ST1). Thereby, the ultrasound image is displayed on the display 35. The operator, who performs the measurement process, starts the measurement process using the ultrasound image displayed. Specifically, the operator operates the input circuit 36 to perform the measurement process.

The control circuit 39 is in standby mode until the operator inputs a signal for starting the measurement process via the input circuit 36 (NO in ST2). When the operator operates the input circuit 36 to perform the measurement process, the control circuit 39 receives a measurement process start signal and starts a series of processes for performing the measurement process (YES in ST2).

Upon receipt of the measurement process start signal, the control circuit 39 displays the guide G and the caliper C suitable for the measurement target on the display 35 (ST3).

From among combinations of the caliper C and the guide G displayed on the display 35, the operator selects an optimum set of combinations for measuring the measurement target. The control circuit 39 receives the selection signal provided by the operator through the input circuit 36 (ST4).

The control circuit 39 calculates the size of the guide and the caliper to be displayed according to the display scale of the ultrasound image displayed on the display 35, and changes the size of the guide and the caliper selected (ST5). After that, the control circuit 39 displays the caliper C and the guide G, the display scale of which has been changed, on the ultrasound image displayed on the display 35 (ST6).

The caliper C and the guide G are moved integrally (ST7). The operator moves the caliper C and the guide G by using, for example, a track ball, a mouse, or the like constituting the input circuit 36.

The operator specifies a position serving as the index on the ultrasound image and operates, for example, the trackball to set the guide G at the position of the index. The control circuit 39 moves the guide G on the display 35 according to the operation of the operator (ST8). During this period, the position where the guide G is arranged on the ultrasound image is yet to be determined. Accordingly, regarding the determination of the arrangement position, while controlling the movement of the guide G, the control circuit 39 waits for the next operation of the operator to determine the position of the guide G (NO in ST8).

Having placed the guide G at the position of the index on the ultrasound image by operating, for example, the trackball (YES in ST8), the operator determines the arrangement position of the guide G using, for example, a button provided to the input circuit 36 such as set button. The control circuit 39 receives an input signal from the button and displays the guide G at the position determined on the ultrasound image (ST9).

After the position of the guide G has been determined on the ultrasound image as above, the inclination (angle) of the caliper C and the guide G is set according to the position of the measurement target (ST10). This is because the measurement target is not always displayed horizontally on the display 35. To set the angle, the operator uses, for example, a dial constituting the input circuit 36.

When the setting of the display angle is not performed (NO in ST10), it means that the angle at which the caliper C and the guide G are displayed on the display 35 is acceptable. In this case, the operator is not required to perform the dial operation. When the setting is completed (including the case where the setting of the display angle is not performed) (YES in ST10), the operator determines the display angle of the caliper C and the guide G (ST11 in FIG. 7). Specifically, the control circuit 39 displays the caliper C and the guide G at the set angle in response to a determination signal based on the determination operation by the operator.

After the arrangement position of the guide G is arranged on the ultrasound image and the angle between the guide G and the caliper C is arranged in an appropriate positional relationship in relation to the measurement target, the operator then adjusts the arrangement position of the caliper C (ST12). As an actual operation, for example, the arrangement position of the caliper C is adjusted using the trackball. In this case, the role of the trackball used to move the guide G changes to the role of adjusting the arrangement position of the caliper C as the arrangement position of the guide G has been determined.

The adjustment of the arrangement position of the caliper C is not only to pinch the blood vessel wall so that the blood vessel wall can be measured as described above, but it also includes the adjustment of the angle of the caliper C according to the angle of the blood vessel wall.

Having received a signal indicating that the operator starts operating the track ball (YES in ST12), the control circuit 39 moves the display of the caliper C on the ultrasound image according to the signal and adjusts the arrangement position of the caliper C (ST13). The arrangement position of the caliper C is kept adjusted until the caliper C is placed at a position suitable for measurement, (NO in ST14). When the operator performs a process to determine the arrangement position of the caliper C such as pressing of the set button (YES in ST14), the arrangement position of the caliper C is finally determined (ST15).

When the guide G is placed at the position of the index, the caliper C is arranged at the measurement target. At this time, it may not be necessary to further adjust the arrangement position of the caliper C (NO in ST12). In this case, the arrangement position of the caliper is determined at the position (ST15).

When the caliper C is placed at the final position in the measurement target, the measurement target is measured (ST16, and the measurement result is displayed on the display 35 (ST17).

As described above, when a measurement target is measured on a medical image, the caliper is automatically arranged in the measurement target simply by arranging the guide at the position of the index. Thus, the measurement process can be performed quickly and easily.

In the embodiment described above, the caliper and the guide are used for an ultrasound image displayed on the ultrasound image diagnosis apparatus. However, the caliper and the guide of the embodiment may also be applied to a medical image processing apparatus capable of displaying medical images including ultrasound images captured by a variety of modalities.

With reference to FIGS. 2 and 3 illustrating a blood vessel such as the carotid artery as a measurement target at the site to be diagnosed, a description is given of the arrangement of the guide at the position of the index and the arrangement of the caliper at the measurement target according to the arrangement of the guide. However, the application of the caliper and the guide is not limited to the blood vessel. The caliper and the guide can also be applied to the case where the heart is to be measured by, for example, placing a guide at the apex of the heart to figure out a site indicated by the caliper arranged at a position separated therefrom by a predetermined distance.

Further, with reference to FIG. 5, an example is described in which a predetermined distance between the guide and the caliper is defined on the time axis. While, in the example of FIG. 5, the guide and the caliper are applied to the velocity of blood flow, they can also be applicable to electrocardiogram waveform, for example. For example, the caliper and the guide described above can be applied to the setting of the diastolic heart beat time phase referring to the end systole based on the end diastole specified by R waves in the electrocardiogram waveform upon acquiring parameters required for early diagnosis of heart disease.

As described above, upon displaying the caliper and the guide, the size thereof is adjusted so as to be matched with the display scale of the medical image displayed as advance preparation. Such process is performed not only for advance preparation. For example, after the caliper and the guide are displayed on a medical image, each time the display scale of the medical image is enlarged or contracted and changed, the distance between the caliper and the guide is adjusted. Thereby, the relative positional relationship between the caliper and the guide does not change in any display scale. Thus, the operator is less likely to mistake the size of the measurement target.

In the above description, it is assumed that the distance between the caliper and the guide is defined in advance. However, even if the measurement target is in the same diagnostic site, for example, the distance between the caliper and the guide can vary depending on depending on whether the subject is an adult or a child, race, sex, or the like. Therefore, the distance between the caliper and the guide may be adjustable by the operator. In this case, the distance can be automatically changed based on conditions such as patient ID.

Alternatively, if there is an examination performed based on certain statistics collected for each condition such as race, sex, age, and the like, when the examination is selected, the distance between the caliper and the guide may be changed according to the conditions. Further, when the measurement value in the measurement target has a predetermined relationship with another measurement item, the distance between the caliper and the guide can be changed according to the other measurement item.

It is also possible to define and store a plurality of different patterns for the distance between the caliper and the guide. In this case, the operator can appropriately select and use a suitable pattern related to the distance between the caliper and the guide according to the subject.

While certain embodiments have been described, these embodiments have been presented by way of example only, and are not intended to limit the scope of the inventions. Indeed, the novel embodiments described herein may be embodied in a variety of other forms; Further, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound image diagnosis apparatus, comprising:
a display configured to display an ultrasound image generated based on an echo signal of ultrasound waves transmitted to a site to be diagnosed; and
processing circuitry configured to measure a measurement target on the ultrasound image of the site to be diagnosed displayed on the display, wherein the processing circuitry performs
a definition function to define a distance between a caliper used to measure the measurement target and a guide used to arrange the caliper at a position of the measurement target,
a display control function to control display of the caliper and the guide arranged to be separated by the defined distance such that the caliper and the guide are integrally movable on the ultrasound image, and
a measurement function to measure the measurement target using the caliper.

2. The ultrasound image diagnosis apparatus of claim 1, wherein the distance between the caliper and the guide is defined in advance according to the measurement target.

3. The ultrasound image diagnosis apparatus of claim 2, wherein the distance between the caliper and the guide is defined based on an actual measurement value of the measurement target.

4. The ultrasound image diagnosis apparatus as claimed in claim 1, wherein the definition function defines an angle between the caliper used to measure the measurement target and the guide used to arrange the caliper at the position of the measurement target.

5. The ultrasound image diagnosis apparatus as claimed in claim 1, wherein the caliper is displayed as a pair of parallel lines and the guide is displayed as a circular mark separated from the pair of parallel lines by the defined distance.

6. The ultrasound image diagnosis apparatus as claimed in claim 1, wherein the caliper is displayed as a pair of crosses and the guide is displayed as a circular mark separated from the pair of crosses by the defined distance.

7. An ultrasound image diagnosis apparatus, comprising:
a display configured to display an ultrasound image generated based on an echo signal of ultrasound waves transmitted to a site to be diagnosed; and
processing circuitry configured to measure a measurement target on the ultrasound image of the site to be diagnosed displayed on the display, wherein the processing circuitry performs
a definition function to define a distance on a time axis between a caliper used to measure the measurement target and a guide used to arrange the caliper at a position of the measurement target,
a display control function to control display of the caliper and the guide arranged to be separated by the defined distance such that the caliper and the guide are integrally movable on the ultrasound image, and
a measurement function to measure the measurement target using the caliper.

8. The ultrasound image diagnosis apparatus of claim 7, wherein the distance between the caliper and the guide is defined in advance according to the measurement target.

9. The ultrasound image diagnosis apparatus of claim 8, wherein the distance between the caliper and the guide is defined based on an actual measurement value of the measurement target.

10. A medical image processing apparatus, comprising:
a display configured to display a medical image generated based on internal information of a subject acquired at a site to be diagnosed; and
processing circuitry configured to measure a measurement target on the medical image of the site to be diagnosed displayed on the display, wherein the processing circuitry performs
a definition function to define a distance between a caliper used to measure the measurement target and a guide used to arrange the caliper at a position of the measurement target,
a display control function to control display of the caliper and the guide arranged to be separated by the defined distance such that the caliper and the guide are integrally movable on the medical image, and
a measurement function to measure the measurement target using the caliper.

11. The medical image processing apparatus as claimed in claim 10, wherein the definition function defines an angle between the caliper used to measure the measurement target and the guide used to arrange the caliper at the position of the measurement target.

12. The medical image processing apparatus as claimed in claim 10, wherein the caliper is displayed as a pair of parallel lines and the guide is displayed as a circular mark separated from the pair of parallel lines by the defined distance.

13. The medical image processing apparatus as claimed in claim 10, wherein the caliper is displayed as a pair of crosses and the guide is displayed as a circular mark separated from the pair of crosses by the defined distance.

14. A computer program product comprising a non-transitory computer-usable medium having computer-readable program codes that, when executed, cause a computer to:
display a medical image generated based on internal information of a subject acquired at a site to be diagnosed;
move a caliper used to measure a measurement target and a guide used to arrange the caliper at a position of the measurement target integrally on the medical image, wherein a distance between the caliper and the guide is defined, to arrange the guide at a position of an index, and display the caliper at a position separated from the guide by the defined distance; and
measure the measurement target using the caliper.

15. The computer program product as claimed in claim 14, wherein the caliper used to measure the measurement target and the guide used to arrange the caliper at the position of the measurement target are oriented at an angle set by a user.

16. The computer program product as claimed in claim 14, wherein the caliper is displayed as a pair of parallel lines and the guide is displayed as a circular mark separated from the pair of parallel lines by the defined distance.

17. The computer program product as claimed in claim 14, wherein the caliper is displayed as a pair of crosses and the guide is displayed as a circular mark separated from the pair of crosses by the defined distance.

* * * * *